(12) United States Patent
Karunasiri

(10) Patent No.: US 7,254,449 B2
(45) Date of Patent: Aug. 7, 2007

(54) SYSTEMS AND METHODS FOR PROVIDING POWER TO ONE OR MORE IMPLANTABLE DEVICES

(76) Inventor: Rankiri Tissa Karunasiri, 28829 W. Carnation Ct., Castaic, CA (US) 91384

(*) Notice: Subject to any disclaimer, the term of this patent is extended or adjusted under 35 U.S.C. 154(b) by 0 days.

(21) Appl. No.: 11/341,066

(22) Filed: Jan. 27, 2006

(65) Prior Publication Data
US 2006/0149340 A1    Jul. 6, 2006

Related U.S. Application Data

(63) Continuation-in-part of application No. 10/209,054, filed on Jul. 31, 2002, now Pat. No. 7,016,738.

(51) Int. Cl.
*A61N 1/08* (2006.01)

(52) U.S. Cl. .............. 607/61; 607/33; 607/34; 607/65; 607/57

(58) Field of Classification Search ........... 607/33, 607/34, 61, 65, 66, 56, 57; 330/124 R, 124 D, 330/295
See application file for complete search history.

(56) References Cited

U.S. PATENT DOCUMENTS

| | | |
|---|---|---|
| 3,751,605 A | 8/1973 | Michelson |
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |
| 4,360,019 A | 11/1982 | Portner et al. |
| 4,400,590 A | 8/1983 | Michelson |
| 4,487,603 A | 12/1984 | Harris |
| 4,532,930 A | 8/1985 | Crosby et al. |
| 4,562,751 A | 1/1986 | Nason et al. |
| 4,592,359 A | 6/1986 | Galbraith |

(Continued)

FOREIGN PATENT DOCUMENTS

| | | |
|---|---|---|
| WO | WO 01/82398 A1 | 1/2001 |
| WO | WO 03/005465 A1 | 1/2003 |

*Primary Examiner*—Carl Layno
*Assistant Examiner*—Eugene Wu
(74) *Attorney, Agent, or Firm*—Travis K. Laird; AdvantEdge Law Group, LLC

(57) ABSTRACT

Systems and methods for providing a power signal to one or more implantable devices include a number of dynamic range amplifiers each having a multiplicity of output drivers. Each of the output drivers is configured to generate an output signal. The systems and methods further include control circuitry configured to select at least one of the amplifiers to provide a number of output signals used to generate the power signal that is to be provided to the one or more implantable devices. The control circuitry is further configured to disable the output drivers corresponding to a remaining number of amplifiers. A matching circuit is configured to generate the power signal based on the output signals provided by the at least one selected amplifier. The systems and methods further include means to transmit the power signal to the one or more implantable devices.

18 Claims, 14 Drawing Sheets

U.S. PATENT DOCUMENTS

| | | | |
|---|---|---|---|
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,819,647 A | 4/1989 | Byers et al. | |
| 4,865,845 A | 9/1989 | Eckenhoff et al. | |
| 4,947,844 A | 8/1990 | McDermott | |
| 5,057,318 A | 10/1991 | Magruder et al. | |
| 5,059,423 A | 10/1991 | Magruder et al. | |
| 5,080,653 A | 1/1992 | Voss et al. | |
| 5,083,094 A * | 1/1992 | Forsberg | 330/124 R |
| 5,097,122 A | 3/1992 | Colman et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,312,439 A | 5/1994 | Loeb | |
| 5,501,703 A | 3/1996 | Holsheimer | |
| 5,690,693 A * | 11/1997 | Wang et al. | 607/61 |
| 5,702,431 A * | 12/1997 | Wang et al. | 607/61 |
| 5,728,396 A | 3/1998 | Peery et al. | |
| 5,824,022 A | 10/1998 | Zilberman et al. | |
| 5,872,481 A * | 2/1999 | Sevic et al. | 330/51 |
| 5,938,688 A | 8/1999 | Schiff | |
| 6,016,449 A | 1/2000 | Fischell et al. | |
| 6,047,214 A * | 4/2000 | Mueller et al. | 607/61 |
| 6,051,017 A | 4/2000 | Loeb et al. | |
| 6,129,753 A | 10/2000 | Kuzma | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,272,382 B1 | 8/2001 | Faltys et al. | |
| 6,280,873 B1 | 8/2001 | Tsukamoto | |
| 6,308,101 B1 | 10/2001 | Faltys et al. | |
| 6,368,315 B1 | 4/2002 | Gillis et al. | |
| 6,381,496 B1 | 4/2002 | Meadows et al. | |
| 6,458,171 B1 | 10/2002 | Tsukamoto | |
| 6,477,425 B1 * | 11/2002 | Nowick et al. | 607/61 |
| 6,487,446 B1 | 11/2002 | Hill et al. | |
| 6,516,227 B1 | 2/2003 | Meadows et al. | |
| 6,553,263 B1 * | 4/2003 | Meadows et al. | 607/61 |
| 6,620,151 B2 | 9/2003 | Blischak et al. | |
| 6,666,845 B2 | 12/2003 | Hooper et al. | |
| 6,738,432 B2 * | 5/2004 | Pehlke et al. | 375/300 |
| 6,740,072 B2 | 5/2004 | Starkweather et al. | |
| 6,760,626 B1 | 7/2004 | Boveja | |
| 6,765,439 B2 * | 7/2004 | Choi | 330/129 |
| 6,770,067 B2 | 8/2004 | Lorenzen et al. | |
| 6,782,244 B2 * | 8/2004 | Steel et al. | 455/127.1 |
| 6,791,407 B2 * | 9/2004 | Grebennikov et al. | 330/133 |
| 7,064,606 B2 * | 6/2006 | Louis | 330/124 R |
| 7,107,103 B2 * | 9/2006 | Schulman et al. | 607/61 |
| 2001/0046625 A1 | 11/2001 | Ruth, II et al. | |
| 2001/0053476 A1 | 12/2001 | Ruth et al. | |
| 2002/0188333 A1 * | 12/2002 | Nowick et al. | 607/61 |
| 2003/0078634 A1 * | 4/2003 | Schulman et al. | 607/61 |
| 2003/0191504 A1 * | 10/2003 | Meadows et al. | 607/33 |

\* cited by examiner

SYSTEMS AND METHODS FOR PROVIDING POWER TO ONE OR MORE IMPLANTABLE DEVICES

RELATED APPLICATIONS

The present application is a continuation-in-part application of U.S. application Ser. No. 10/209,054, filed Jul. 31, 2002, now U.S. Pat. No. 7,016,738, which application is incorporated herein by reference in its entirety.

BACKGROUND

Radio-frequency (RF) powered implantable stimulators and battery powered implantable stimulators are described in the art. See, for instance, U.S. Pat. No. 5,193,539 ("Implantable Microstimulator); U.S. Pat. No. 5,193,540 ("Structure and Method of Manufacture of an Implantable Microstimulator"); U.S. Pat. No. 5,312,439 ("Implantable Device Having an Electrolytic Storage Electrode"); U.S. Pat. No. 6,185,452 ("Battery-Powered Patient Implantable Device"); U.S. Pat. Nos. 6,164,284 and 6,208,894 (both titled "System of Implantable Device for Monitoring and/or Affecting Body Parameters"). Each of these patents is incorporated herein by reference in its respective entirety.

Implantable stimulators may be used to treat a variety of medical disorders. For example, to overcome sensorineural hearing loss, numerous cochlear implant systems, also referred to as implantable cochlear stimulator (ICS) systems, have been developed. These devices seek to bypass the hair cells in the cochlea, which are essential to hearing but which may not functioning properly, by presenting electrical stimulation directly to the auditory nerve fibers. This leads to the perception of sound in the brain and at least partial restoration of hearing function. To facilitate direct stimulation of the auditory nerve fibers, an array of electrodes may be implanted in the cochlea. A sound processor processes an incoming sound and translates it into electrical stimulation pulses applied by these electrodes to directly stimulate the auditory nerve.

A typical implantable stimulator is intended to remain permanently in the body of a patient once it is implanted. For this reason, many stimulation systems include one or more external devices configured to communicate with and support the stimulator or other device that is implanted within the patient. For example, some exemplary cochlear implant systems include a behind-the-ear (BTE) signal processor that may be positioned behind the ear and used to support an implanted stimulator.

The external portion of many stimulation systems includes a radio frequency (RF) power amplifier that is configured to provide power to the portion of the stimulation system that is implanted within the patient. The external portion will be specifically designed to meet the power requirements of the implanted device.

SUMMARY

Systems for providing a power signal to one or more implantable devices include a number of dynamic range amplifiers each having a multiplicity of output drivers. Each of the output drivers is configured to generate an output signal. The systems further include control circuitry configured to select at least one of the amplifiers to provide a number of output signals used to generate the power signal that is to be provided to the one or more implantable devices. The control circuitry is further configured to disable the output drivers corresponding to a remaining number of amplifiers. A matching circuit is configured to generate the power signal based on the output signals provided by the at least one selected amplifier.

Methods of providing a power signal to one or more implantable devices include providing a number of dynamic range amplifiers each comprising a multiplicity of output drivers. Each of the output drivers is configured to generate an output signal. The method further includes selecting at least one of the amplifiers to provide a number of output signals used to generate the power signal, disabling the output drivers corresponding to a remaining number of amplifiers; and generating the power signal based on the output signals provided by the at least one selected amplifier.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

As described above, the external portion of many implantable stimulation systems includes a radio frequency (RF) power amplifier that is configured to provide power to the portion of the stimulation system that is implanted within the patient. The external portion will be specifically designed to meet the power requirements of the implanted device. However, it may sometimes be desired to use the external portion of the system with different implantable devices in different patients. In other implementations, there may be two or more implanted devices that compose the stimulation system. In such cases, it is desirable for the external RF power amplifier to be able to provide power to some or all of the different implantable devices with which it may be deployed. However, each of these implantable devices may have significantly different power requirements.

Consequently, systems and methods for providing power over a wide dynamic range to one or more implantable devices are described herein. A number of dynamic range amplifiers are configured to generate a multiplicity of output signals with a multiplicity of output drivers. Control circuitry is configured to select one of the amplifiers to provide a number of output signals used to generate the power signal that is to be provided to the one or more implantable devices. The control circuitry is further configured to disable the output drivers corresponding to a remaining number of amplifiers. A matching circuit is configured to generate the power signal based on the output signals provided by the selected amplifier.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
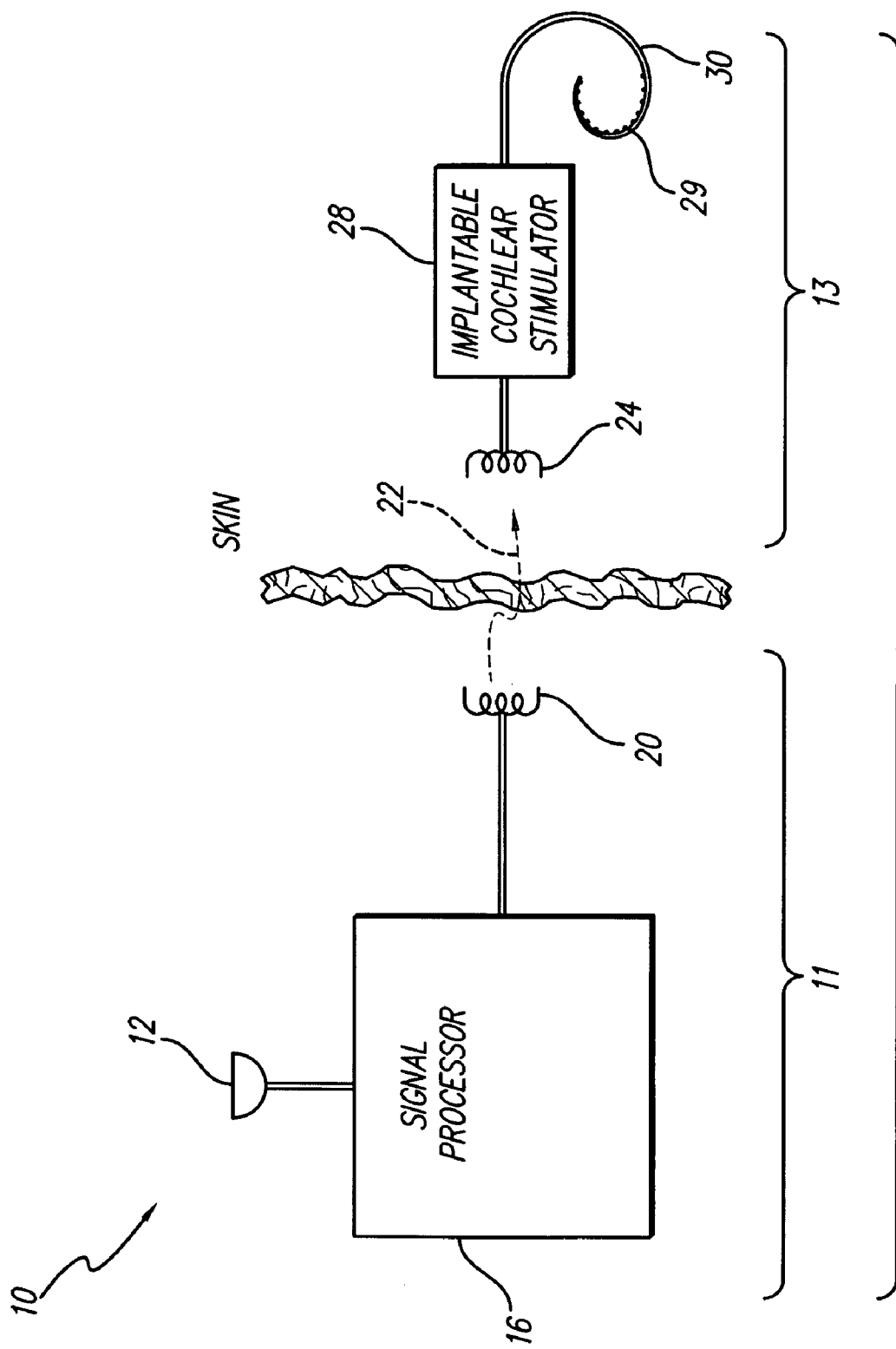
FIG. 1 shows an exemplary cochlear implant system according to principles described herein.

FIG. 1 shows an exemplary cochlear implant system (10) that may be used as a stimulator in accordance with the present methods and systems. Exemplary cochlear implant systems suitable for use as described herein include, but are not limited to, those disclosed in U.S. Pat. Nos. 4,400,590; 4,532,930; 4,592,359; 4,947,844; and 5,824,022; 6,219,580; 6,272,382; and 6,308,101. All of these listed patents are incorporated herein by reference in their respective entireties.

The cochlear implant system (10) includes an external signal processor portion (11) and an implanted cochlear stimulation portion (13). The signal processor portion (11) may include a signal processor (SP) (16), a microphone (12), and/or additional circuitry as best serves a particular application. The cochlear stimulation portion (13) may include an implantable cochlear stimulator (ICS) (28), a number of electrodes (29) disposed on a lead (30), and/or additional circuitry as best serves a particular application. The components within the signal processor portion (11) and the cochlear stimulation portion (13) will be described in more detail below.

The microphone (12) of FIG. 1 is configured to sense acoustic signals and convert such sensed signals to corresponding electrical signals. The electrical signals are sent to the SP (16) over an electrical or other suitable link. Alternatively, the microphone (12) may be connected directly to, or integrated with, the SP (16). The SP (16) processes these converted acoustic signals in accordance with a selected speech processing strategy to generate appropriate control signals or stimulation parameters for controlling the ICS (28). These stimulation parameters may specify or define the polarity, magnitude, location (i.e., which electrode pair or electrode group receive the stimulation current), and timing (i.e., when the stimulation current is to be applied to a particular electrode pair) of the stimulation current that is generated by the ICS (28).

The lead (30) of FIG. 1 is adapted to be inserted within a duct of the cochlea. As shown in FIG. 1, the lead (30) includes a multiplicity of electrodes (29), e.g., sixteen electrodes, disposed along its length. Each of the electrodes (29) is individually coupled to the ICS (28). The lead (30) may be substantially as shown and described in U.S. Pat. No. 4,819,647 or 6,129,753, each of which is incorporated herein by reference in its respective entirety. Electronic circuitry within the ICS (28) is configured to apply stimulation current to selected pairs or groups of the individual electrodes (29) included within the lead (30) in accordance with a specified stimulation pattern controlled by the SP (16).

As mentioned, ICS (28) and lead (30) may be implanted within the patient while the signal processor (16) and the microphone (12) are configured to be located outside the patient. Hence, the ICS (28) and the SP (16) may be transcutaneously coupled via a suitable data or communications link (22). The communications link (22) allows power and control signals to be sent from the SP (16) to the ICS (28). In some embodiments, data and status signals may also be sent from the ICS (28) to the SP (16).

The external and implantable portions of the cochlear implant system (10) may each include one or more coils configured to transmit and receive power and/or control signals via the data link (22). For example, the external portion (11) of the cochlear implant system (10) may include an external coil (20) and the implantable portion of the cochlear implant system (13) may include an implantable coil (24). The external coil (20) and the implantable coil (24) may be inductively coupled to each other, thereby allowing data and power signals to be wirelessly transmitted between the external portion and the implantable portion of the cochlear implant system (10).

Figure 2:
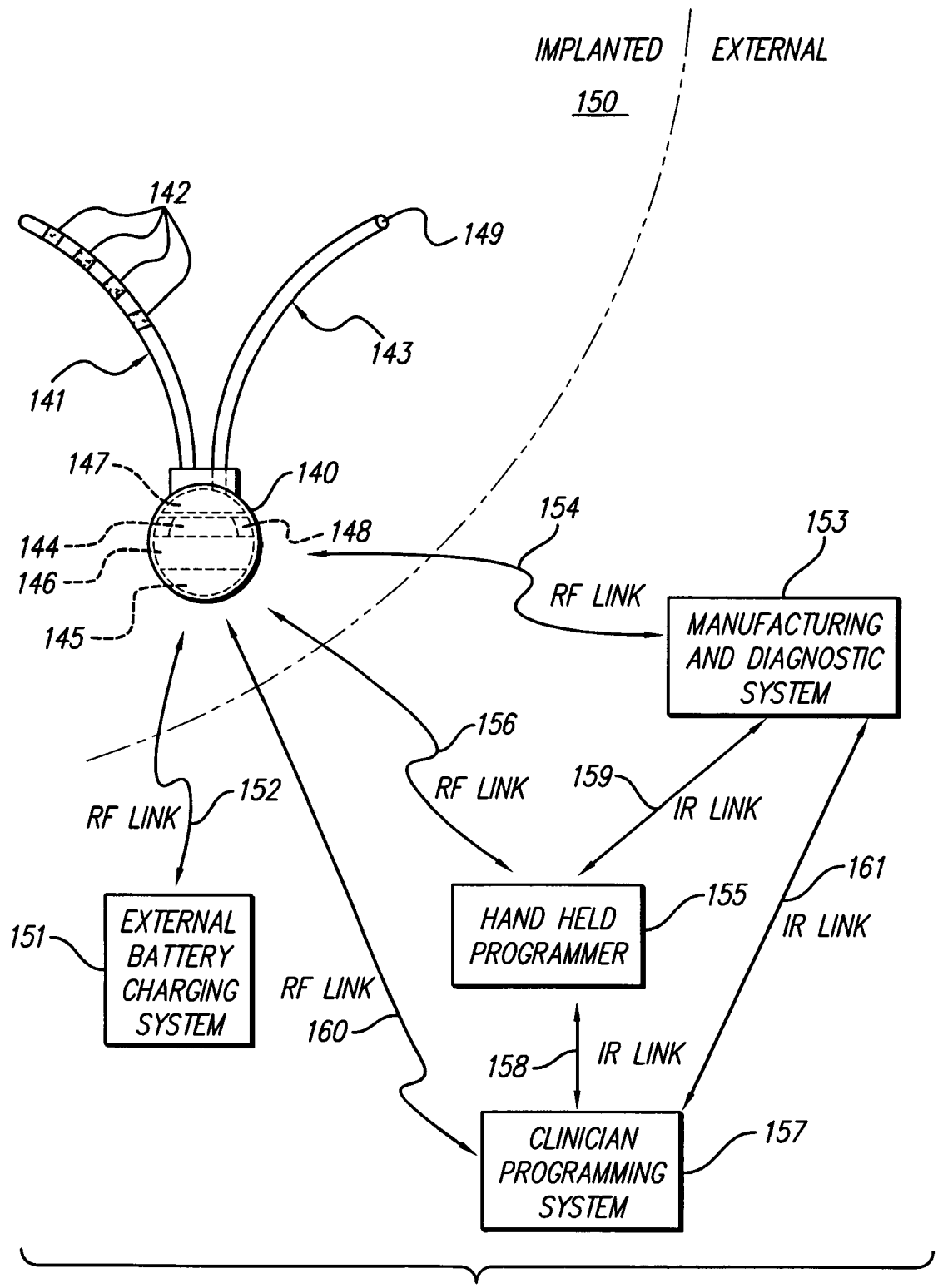
FIG. 2 illustrates an exemplary stimulator that may be implanted within a patient and used to apply a stimulus to a stimulation site according to principles described herein.

The cochlear implant system (10) described in connection with FIG. 1 is merely illustrative of the many types of stimulators that may be used to apply a stimulus to one or more stimulation sites within a patient to treat a wide variety of medical conditions. For example, FIG. 2 illustrates an exemplary stimulator (140) that may be implanted within a patient (150) and used to apply a stimulus to a stimulation site, e.g., an electrical stimulation of the stimulation site, an infusion of one or more drugs at the stimulation site, or both. The electrical stimulation function of the stimulator (140) will be described first, followed by an explanation of the possible drug delivery function of the stimulator (140). It will be understood, however, that the stimulator (140) may be configured to provide only electrical stimulation, only a drug stimulation, both types of stimulation or any other type of stimulation as best suits a particular patient.

The exemplary stimulator (140) shown in FIG. 2 is configured to provide electrical stimulation to a stimulation site within a patient and may include a lead (141) having a proximal end coupled to the body of the stimulator (140). The lead (141) also includes a number of electrodes (142) configured to apply an electrical stimulation current to a stimulation site. The lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) may be thin (e.g., less than 3 millimeters in diameter) such that the lead (141) may be positioned near a stimulation site. In some alternative examples, the stimulator (140) is leadless.

As illustrated in FIG. 2, the stimulator (140) includes a number of components. It will be recognized that the stimulator (140) may include additional and/or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their respective entireties. Other battery construction techniques that may be used to make a power source (145) include those shown, e.g., in U.S. Pat. Nos. 6,280,873; 6,458,171, and U.S. Publications 2001/0046625 A1 and 2001/0053476 A1, all of which are incorporated herein by reference in their respective entireties. Recharging can be performed using an external charger.

The stimulator (140) may also include a coil (148) configured to receive and/or emit a magnetic field (also referred to as a radio frequency (RF) field) that is used to communicate with, or receive power from, one or more external devices (e.g., 151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into the stimulation site.

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

Additionally, if multiple external devices are used in the treatment of a patient, there may be some communication among those external devices, as well as with the implanted stimulator (140) and/or other implanted devices. Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce multipolar stimulation including, but not limited to, bipolar or tripolar stimulation.

The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., burst on time and burst off time), duty cycle or burst repeat interval, ramp on time, and ramp off time of the stimulation current that is applied to the stimulation site.

The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, continuous, or bolus. An exemplary, but not exclusive, intermittent drug infusion rate includes a 24 hour repeating cycle with 8 hours of continuous drug infusion followed by 16 hours of non-infusion. Another example of an intermittent drug infusion rate is a multi-day cycle in which the infusion rate varies each day.

Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different types, causes, or symptoms of medical disorders and/or different patients. Thus, in some embodiments, the stimulation parameters may be adjusted by the patient, a clinician, or other user of the stimulator (140) as best serves the particular patient being treated. The stimulation parameters may also be automatically adjusted by the stimulator (140), as will be described below. For example, the stimulator (140) may increase excitement of a stimulation site by applying a stimulation current having a relatively low frequency (e.g., less than 100 Hz). The stimulator (140) may also decrease excitement of a stimulation site by applying a relatively high frequency (e.g., greater than 100 Hz) stimulation current. The stimulator (140) may also, or alternatively, be programmed to apply the stimulation current to a stimulation site intermittently or continuously.

Additionally, the exemplary stimulator (140) shown in FIG. 2 is configured to provide drug stimulation to a patient by applying one or more drugs at a stimulation site within the patient. Hence, to facilitate drug stimulation, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stimulation site. In some embodiments, the stimulator (140) may include multiple catheters (143) and/or pumps (147) for storing and infusing dosages of the one or more drugs at the stimulation site.

The pump (147) or controlled drug release device described herein may include any of a variety of different drug delivery systems. For example, the pump (147) may include a reservoir configured to hold one or more drugs. In some examples, the volume of the reservoir is sufficiently large so as to contain enough drugs for the patient's anticipated lifetime. Alternatively, the reservoir may be refillable, e.g., through a percutaneous injection with a hypodermic needle.

Controlled drug release devices based upon a mechanical or electromechanical infusion pump may be alternatively used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

Hence, as used herein, and in the appended claims, the term "stimulator" will be used broadly to refer to any device that delivers a stimulus, such as an electrical stimulation current, one or, more drugs or other chemical stimulation, thermal stimulation, electromagnetic stimulation, mechanical stimulation, gene infusion, and/or any other suitable stimulation at a stimulation site to treat a psychotic disorder. Thus, the term "stimulator" includes, but is not limited to, a cochlear implant system, stimulator, microstimulator, implantable pulse generator (IPG), spinal cord stimulator (SCS), system control unit, deep brain stimulator, drug pump, or similar device.

Exemplary implantable microstimulators, such as the BION® microstimulator (manufactured by Advanced Bionics® Corporation, Valencia, Calif.), suitable for use as described herein include, but are not limited to, those disclosed in U.S. Pat. Nos. 5,193,539; 5,193,540; 5,312,439; 6,185,452; 6,164,284; 6,208,894; and 6,051,017. Exemplary IPGs suitable for use as described herein include, but are not limited to, those disclosed in U.S. Pat. Nos. 6,381,496; 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

As mentioned, one or more external devices may be configured to recharge the power supply of an implanted stimulator and/or otherwise provide power to the implanted stimulator. The one or more external devices may additionally or alternatively be configured to provide power to other types of implanted devices, e.g., sensors, pacemakers, etc. For this reason, an external device often includes an RF power amplifier configured to generate power that is transmitted to an implanted device. As used herein and in the appended claims, the terms "implanted device" and "implantable device" will be used interchangeably to refer to any device configured to be implanted within a patient including, but not limited to, stimulators, sensors, pacemakers, and pumps, whether or not currently implanted. Likewise, the term "external device" will be used herein and in the appended claims, unless otherwise specifically denoted, to refer to any device configured to be located outside the patient and communicate with and/or provide power to an implanted device. Exemplary external devices include, but are not limited to, behind-the-ear signal processors, external battery charging systems, clinician programming systems, hand held programmers, and manufacturing and diagnostic systems.

In some implementations, it is desirable for an external device to provide power to a number of different implantable devices. As described above, it may sometimes be desirable to use the external device with different implantable devices in different patients. In other implementations, there may be two or more implanted devices that compose the stimulation system. In such cases, it is desirable for the external device to be able to provide power to some or all of the different implantable devices with which it may be deployed. However, each of these implantable devices may have significantly different power requirements. For example, a first implantable device may require 50 to 200 milliwatts (mW) and a second implantable device may require 10 to 90 mW.

Hence, in some examples, an external device as described herein may include a power amplifier configured to provide power over a wide dynamic range. In this manner, as will be described in more detail below, the amplifier may efficiently meet the power requirements of a number of different implantable devices.

Figure 3:
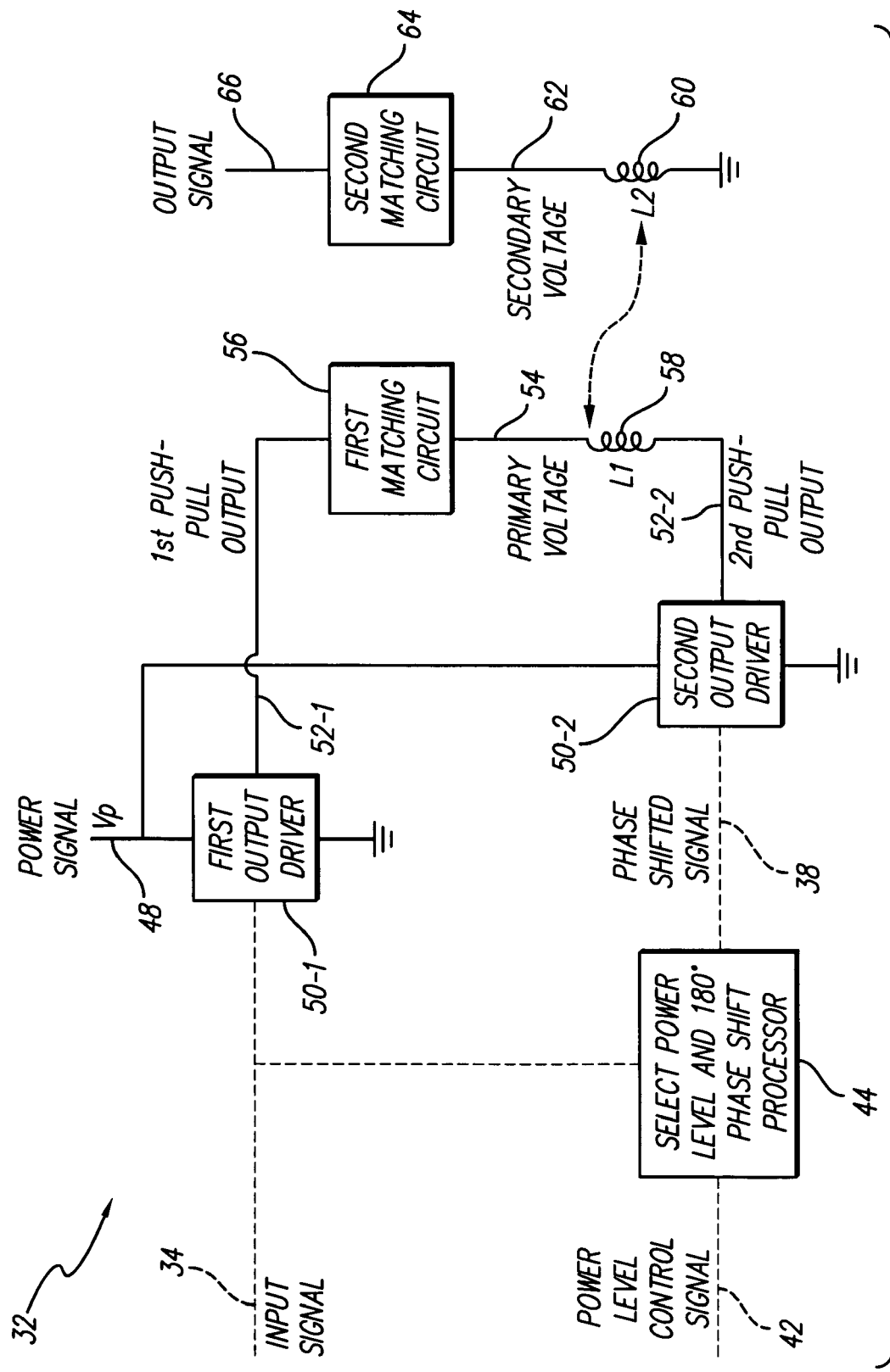
FIG. 3 illustrates a digitally controlled power amplifier according to principles described herein.

A digitally controlled power amplifier (32) with a coarse voltage adjustment providing a wide dynamic range is shown in FIG. 3. The amplifier (32) may be used in any external device to generate a power signal that is to be transmitted to one or more implantable devices, as will be described in more detail below. The amplifier (32) is configured to receive an input power signal with voltage Vp and produce an output signal having a voltage level of either Vp or two times Vp (i.e., 2*Vp), thereby providing a 4:1 (12 dB) coarse power adjustment.

As shown in FIG. 3, an input signal (34) is input into a first output driver (50-1) and a Select Power Level and 180 Degree Phase Shift Processor (referred to herein as a level and phase processor) (44). The input signal (34) is periodic, as shown in FIG. 3, and may include a square wave, for example. Alternatively, the input signal (34) may include any other waveform which sufficiently swings above and below the input thresholds of subsequent processing elements (e.g., the output drivers (50)). The frequency of the input signal (34) may be any suitable frequency as best serves the particular application.

A power level control signal (42) is also input into the level and phase processor (44). The power level control signal (42) determines whether the amplifier (32) is to operate in a high power mode or in a low power mode. In low power mode, the level and phase processor (44) generates a phase shifted signal (38) having an amplitude equal to zero. In high power mode, the level and phase processor (44) generates a 180-degree-phase-shifted signal (38) of the input signal (34). The phase shifted signal (38) generated by the level and phase processor (44) is then input into a second output driver (50-2).

The level and phase processor (44) may include any combination of digital logic, electronic circuitry, software, hardware, and firmware. For example, the level and phase processor (44) may be included within an application specific integrated circuit (ASIC), field-programmable gate array (FPGA), digital signal processor (DSP), or some other type of integrated circuit (IC).

As shown in FIG. 3, a direct current (DC) input power signal having a voltage level represented by Vp is input into both the first and second output drivers (50). In some examples, the input power signal has a number of voltage steps so that the amplifier (32) may operate over a wide dynamic power range. For example, the input power signal may have sixteen steps ranging from 1.25 volts to 3.00 volts. However, it will be recognized that the input power signal may have any number of steps across any voltage range as best serves a particular application.

The first output driver (50-1) generates a first push-pull output signal (52-1) by amplifying the input signal (34) (i.e., generating an amplified replica of the input signal (34) such that the amplitude of the push-pull output signal (52-1) is Vp). The second output driver (50-2) similarly generates a second push-pull output signal (52-2) also with amplitude Vp by amplifying the phase shifted signal (38) generated by the level and phase processor (44). The push-pull signals (52-1) and (52-2) are combined through an in-series primary coil L1 (58) and a first matching network (56) resulting in a primary voltage (54) across the coil (58). The primary voltage (54) is also referred to as a swing voltage. The matching network (56) will be described in more detail below.

The primary coil (58) is inductively coupled with a secondary coil L2 (60), which is in series with a second matching circuit (64). The ratio between the primary coil (58) and the secondary coil (60) is based on the power requirements and sizes of the components within the amplifier (32) and may by 1:1, 1:2, or some other ratio. Due to the signal from the primary coil (58), a secondary voltage (62) is generated across the secondary coil (60) and an output signal (66) is generated by the combination of the coil (60) and the second matching circuit (64).

Figure 4:
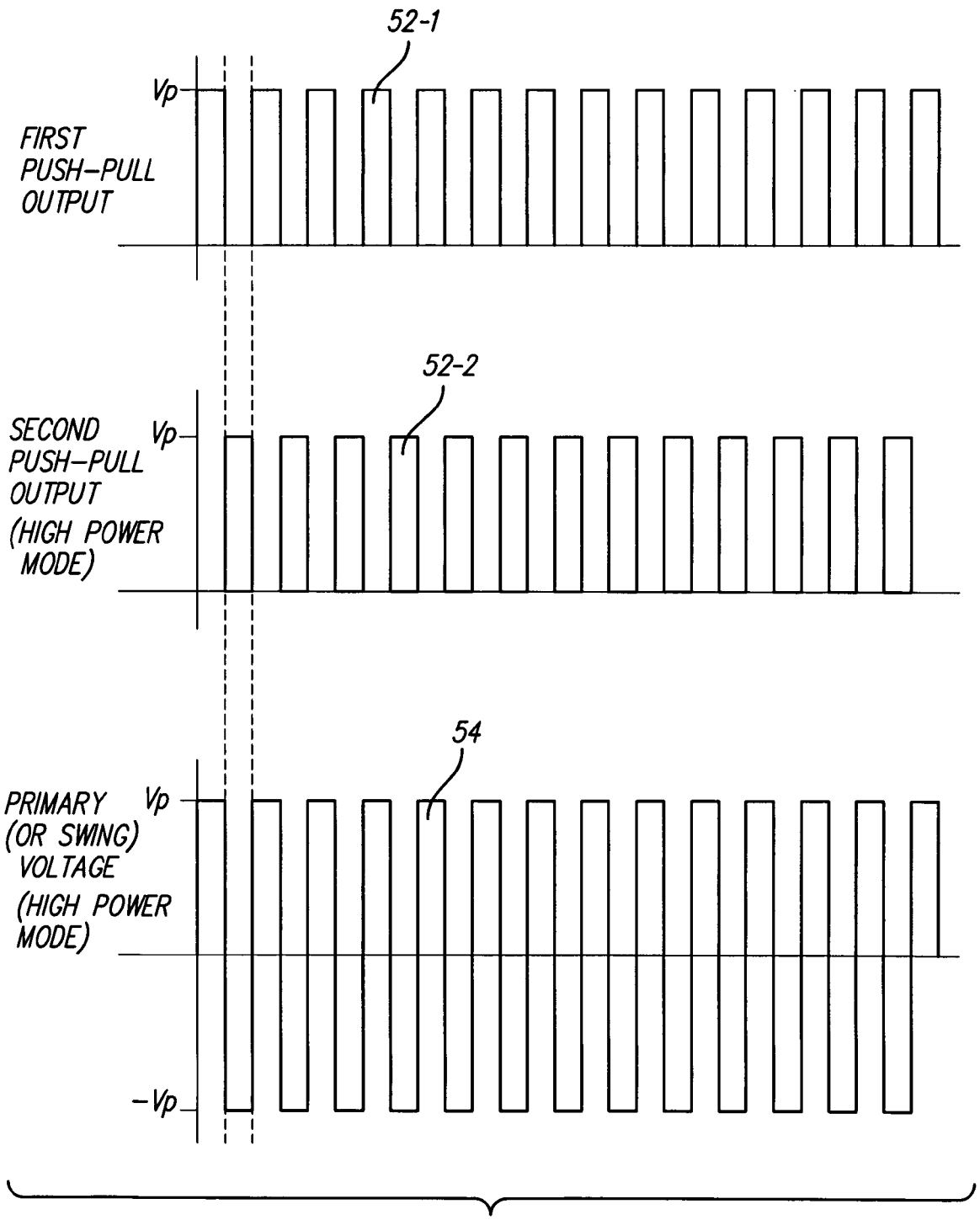
FIG. 4 depicts a first push-pull output, second push-pull output, and resulting primary voltage according to principles described herein.

Plots of the first push-pull output (52-1), second push-pull output (52-2), and resulting primary voltage (54) are shown in FIG. 4. As shown in FIG. 4, the first push-pull output (52-1) swings between zero and a peak voltage level Vp. The second push-pull output (52-2), when operating in high power mode, also swings between zero and Vp, but is shifted 180 degrees in relation to the first push-pull output (52-1). In high power mode, as shown in FIG. 4, the coupling of the primary coil L1 (58; FIG. 3) with the secondary coil L2 (60;

FIG. 3) results in an output signal (54) having a voltage swing of two times Vp (i.e., 2*Vp) across the primary coil L1 (58; FIG. 3).

However, when operating in low power mode, the second push-pull output (52-2) is zero. In this instance, the primary voltage across the primary coil L1 (58; FIG. 3) resembles that of the first push-pull output (52-1).

Hence, the amplifier (32) illustrated in FIG. 3 may be used to selectively output either a low power signal with voltage Vp or a high power signal with a voltage equal to 2*Vp (or four times the power of the low power signal). In some examples, the coarse adjustment in power is controlled by a single digital control input (42; FIG. 3) which switches the amplifier (32) between the low power mode and the high power mode.

Figure 5:
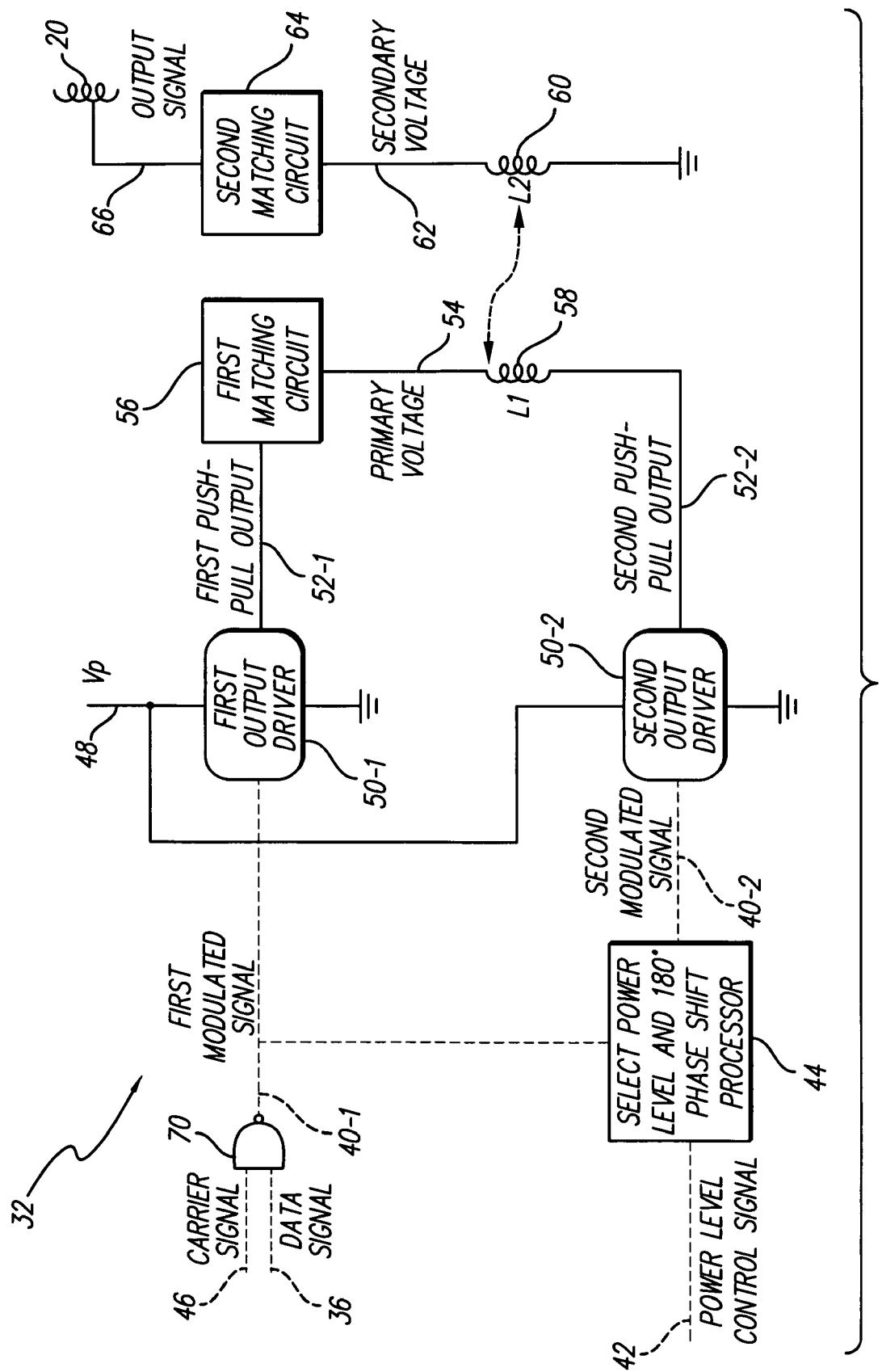
FIG. 5 illustrates an exemplary amplifier configured to amplify a modulated signal including both power and data information according to principles described herein.

As mentioned, an external device may be configured to transmit both data and power to an implantable device. For example, FIG. 5 illustrates an exemplary amplifier (32) configured to amplify a modulated signal including both power and data information. As shown in FIG. 5, a modulated signal including a carrier signal (46) and a data signal (36) is input into the amplifier (32). The data signal (36) includes data that is to be transmitted to the implanted device and may have any frequency as best serves a particular application. An exemplary, but not exclusive, data signal has a frequency of one Megahertz (MHz). The carrier signal (46) may be any carrier signal having any frequency as best serves a particular application. An exemplary, but not exclusive, carrier signal is a square wave having a frequency of 49 MHz.

As shown in FIG. 5, the carrier signal (46) and data signal (36) are modulated using a NAND gate (70). It will be recognized that any combination of digital logic, electronic circuitry, software, hardware, and/or firmware may be used in place of the NAND gate (70) to modulate the data signal (36) onto the carrier signal (46). The modulated signal (40-1) is then input into a first output driver (50-1).

The first modulated signal (40-1) is also input into the level and phase processor (44) along with the power level control signal (42) described in connection with FIG. 3. In low power mode, the level and phase processor (44) generates a second modulated signal (40-2) having an amplitude equal to zero. In high power mode, the second modulated signal (40-2) generated by the level and phase processor (44) is a 180 degree phase shifted replica of the first modulated signal (40-1). The second modulated signal (40-2) generated by the level and phase processor (44) is then input into a second output driver (50-2).

As shown in FIG. 5, a direct current (DC) input power signal having a voltage level represented by Vp is input into both the first and second output drivers (50). The first output driver (50-1) generates a first push-pull output signal (52-1) with amplitude Vp by amplifying the first modulated signal (40-1). The second output driver (50-2) similarly generates a second push-pull output signal (52-2) with amplitude Vp by amplifying the second modulated signal (40-1) generated by the level and phase processor (44). The push-pull output signals (52-1) and (52-2) are combined through an in-series primary coil L1 (58) and a first matching network (56) resulting in a primary voltage (54) across the coil (58). The primary voltage (54) is also referred to as a swing voltage.

The primary coil (58) is inductively coupled with a secondary coil L2 (60), which is in series with a second matching circuit (64). An external or antenna coil (20) is connected to the second matching circuit (64). In response to the field emanating from the primary coil L1 (58), a secondary voltage (62) is generated across the secondary coil (60) and an output signal (66) is generated by the combination of the secondary coil (60) and the second matching circuit (64). As shown in FIG. 5, the output signal (66) may then be transmitted to an implanted device via the external coil (20).

Figure 6:
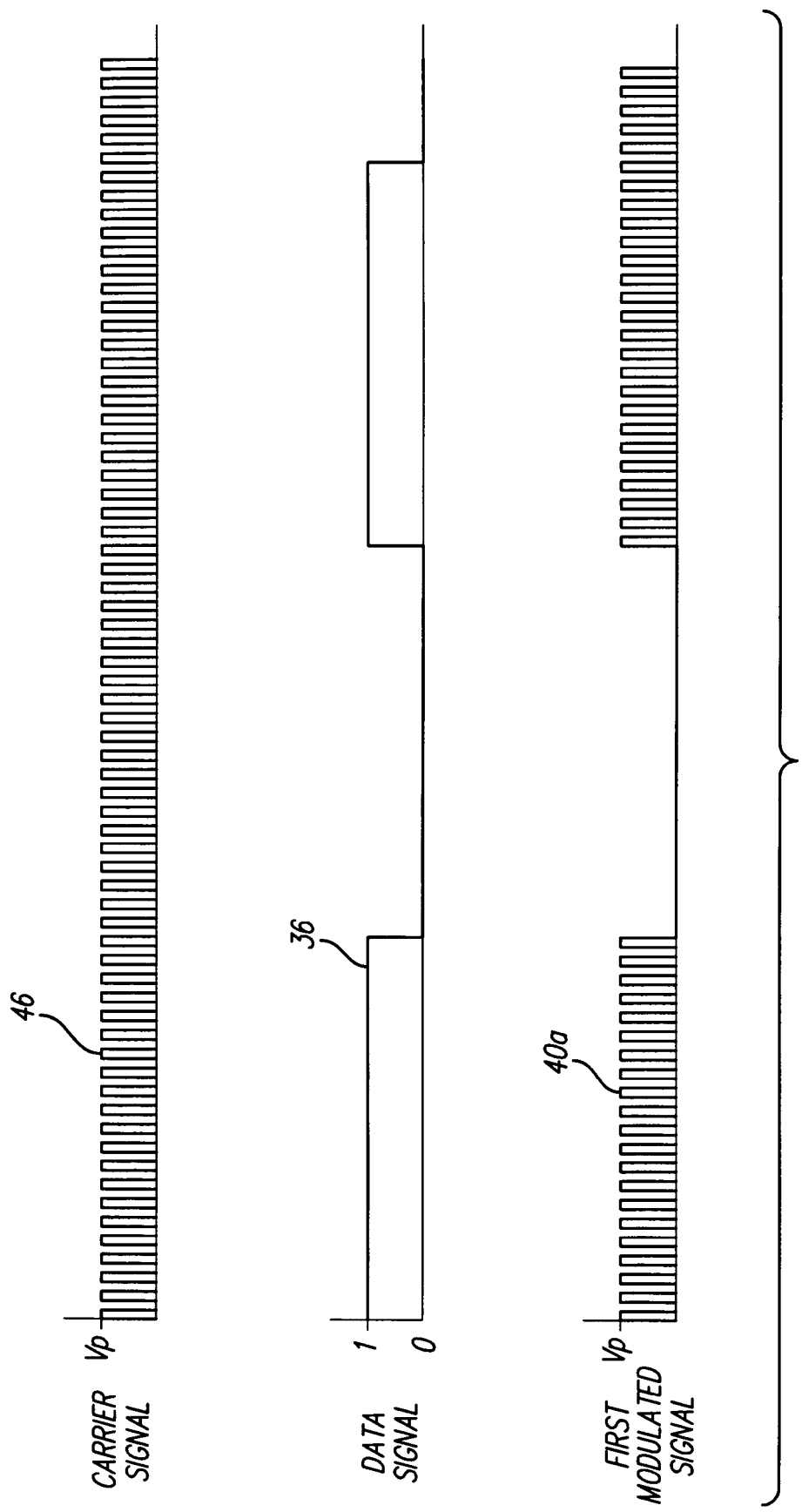
FIG. 6 depicts a carrier signal, data signal, and first modulated signal according to principles described herein.

The carrier signal (46), data signal (36), and first modulated signal (40-1) are shown in FIG. 6. As mentioned, the carrier signal (46) may be a square wave, as shown in FIG. 6. Alternatively, the carrier signal (46) may have any other wave shape as best serves a particular application (e.g., sinusoidal, saw tooth, etc.). Moreover, the carrier signal (46) may have any suitable frequency and amplitude. An exemplary, but not exclusive, frequency of the carrier signal (46) is between 20 Hz and 1000 GHz (e.g., 49 MHz). An exemplary, but not exclusive, amplitude of the carrier signal (46) is substantially equal to the amplitude of the input power signal (Vp).

The data signal (36) shown in FIG. 6 is a digital signal (i.e., a series of ones and zeros) and may have any suitable frequency (e.g., 1 MHz) as best serves a particular application. Hence, as shown in FIG. 6, the first modulated signal (40-1) is zero when the data signal (36) is zero, and is a copy of the carrier signal (46) elsewhere.

Figure 7:
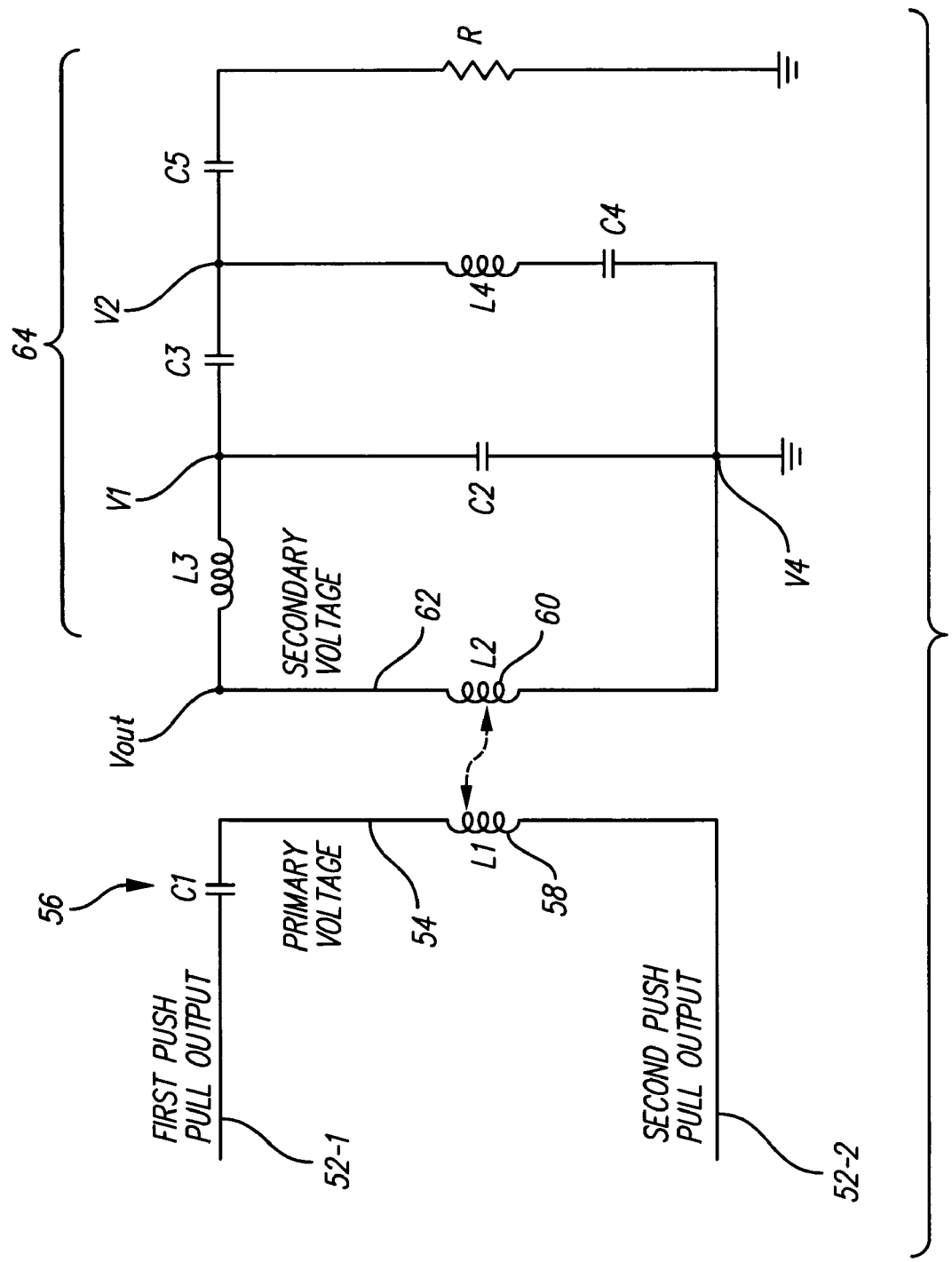
FIG. 7 illustrates exemplary first and second matching circuits that may be used in the amplifier according to principles described herein.

FIG. 7 illustrates exemplary first and second matching circuits (56, 64) that may be used in the amplifier (32; FIG. 5). As shown in FIG. 7, the first matching circuit (56) may include a capacitor C1 connected in series with the primary coil L1 (58) with the series resonance frequency typically, but not exclusively, set to the fundamental frequency of the incoming carrier frequency. The capacitor C1 may have any suitable value, e.g., 500 pF. The second matching circuit (64) may include a number of coils (also referred to as inductors), capacitors, and resistors arranged in the configuration shown in FIG. 7. For example, the second matching circuit (64) may include the secondary coil L2 (60), coils L3 and L4, capacitors C2-C5, and resistor R. Secondary coil L2 (60) is electrically connected between a first node $V_{out}$ and a grounded node V4. Coil L3 is electrically connected between the node $V_{out}$ and another node V1 and may have any suitable value (e.g., 47 nH). Capacitor C2 is electrically connected between the node V1 and the grounded node V4 and may have any suitable value (e.g., 120 pF). The capacitor C3 (e.g., 56 pF) is electrically connected between the node V1 and a node V2. Coil L4 (e.g., 180 nH) and capacitor C4 (e.g., 1200 pF) are electrically connected in series between the node V2 and the node V4. Capacitor C5 (e.g., 56 pF) and a resistor R (e.g., 50 ohms) are electrically connected in series between the node V2 and ground. The resistor R represents any load and may include any resistive element as best serves a particular application. It will be recognized that the components of the matching circuits (56, 64) may vary as best serves a particular application and that their values may also vary as best serves a particular application.

Figure 8A:
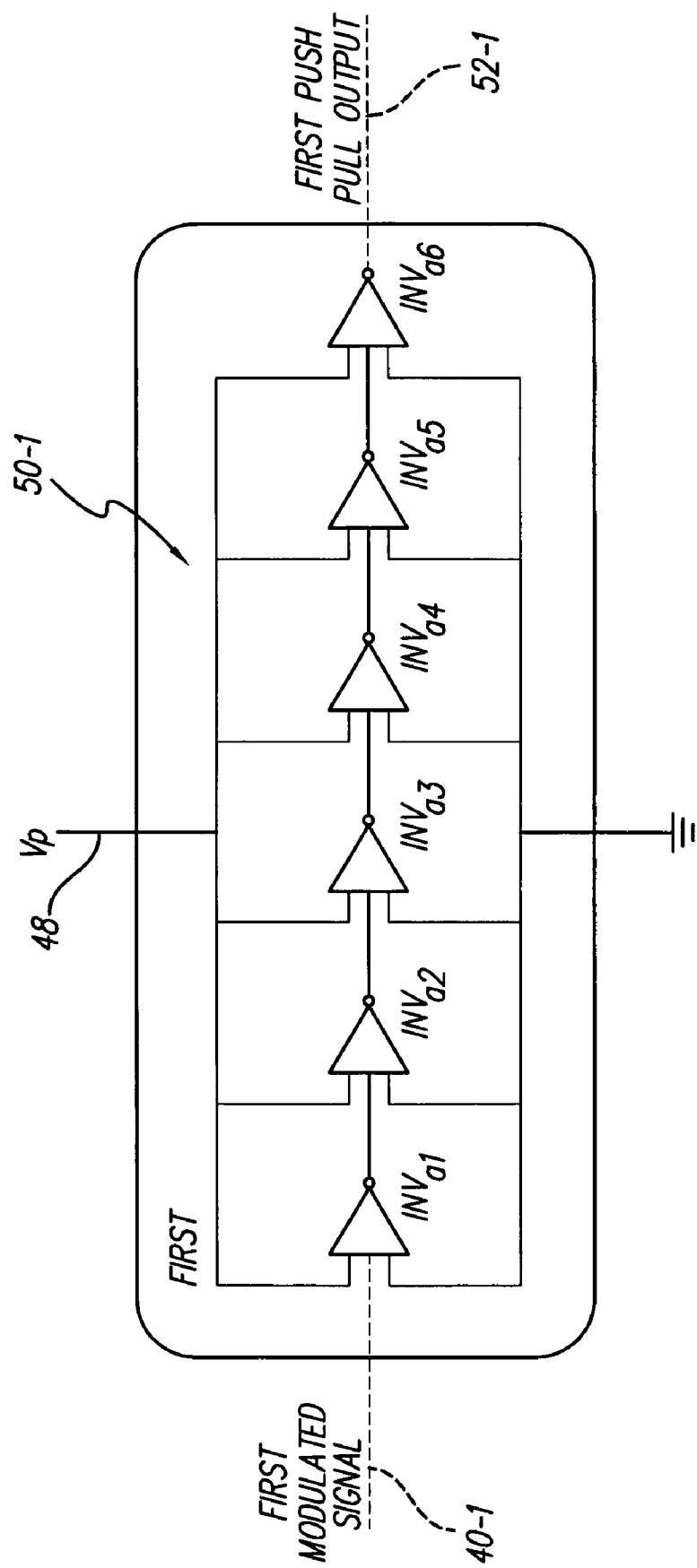
FIG. 8A illustrates an exemplary first output driver that may be used in the amplifier according to principles described herein.
Figure 8B:
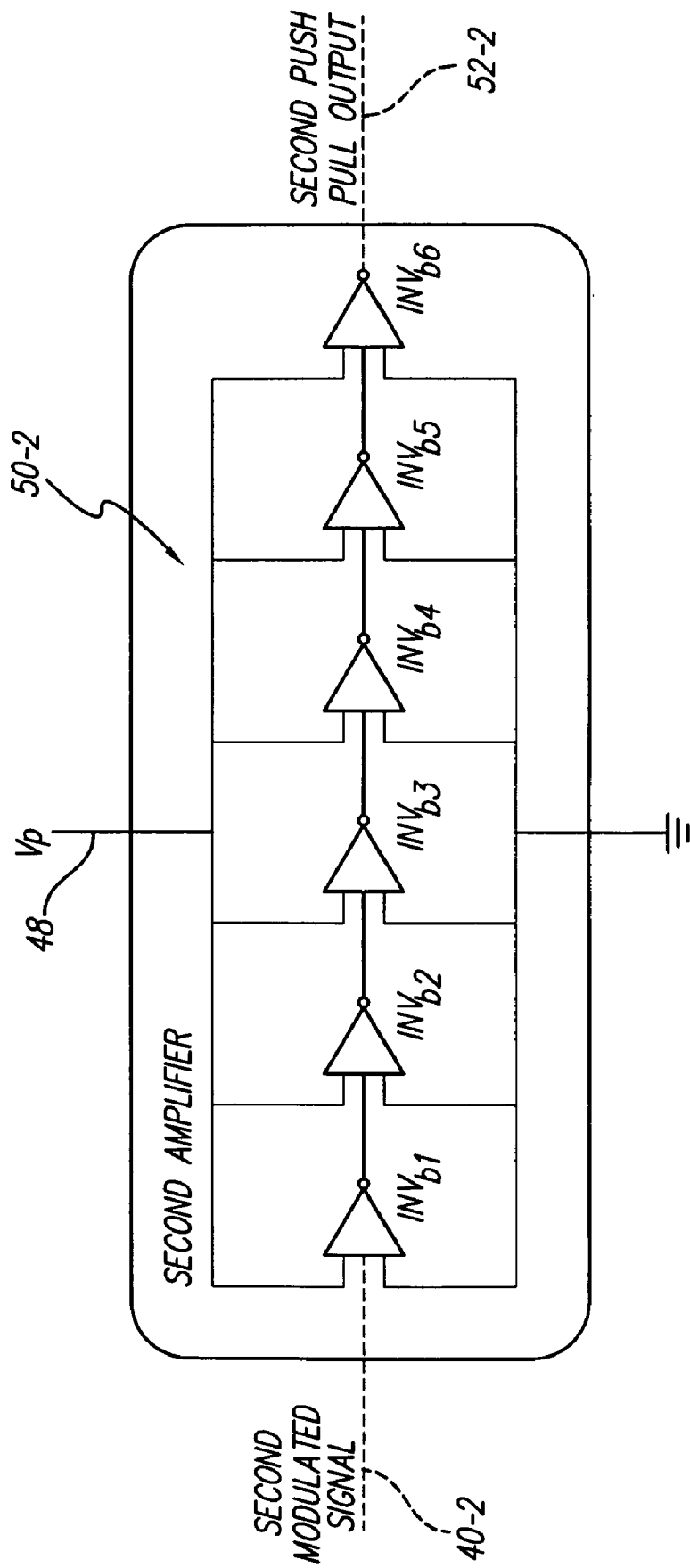
FIG. 8B illustrates an exemplary second output driver that may be used in the amplifier according to principles described herein.

FIG. 8A illustrates an exemplary first output driver (50-1) that may be used in the amplifier (32; FIG. 5). Likewise, FIG. 8B illustrates an exemplary second output driver (50-2) that may be used in the amplifier (32; FIG. 5). As shown in FIG. 8A, the output driver (50-1) receives the first modulated signal (40-1) as a control input and the power signal (48) as a power source. The output driver (50-1) includes a number of inverter stages $INV_{an}$. For example, the output drive (50-1) may include six in-series inverters ($INV_{a1}$, $INV_{a2}$, $INV_{a3}$, $INV_{a4}$, $INV_{a5}$, and $INV_{a6}$). It will be recognized that the output driver (50-1) may include any number of stages as best serves a particular application. Each stage shown in FIG. 8A after the first stage receives the output of the previous stage as a control signal and the power signal (48) as a power source. In this manner, the power of the signal output by each stage increases until the desired amplification of the modulated signal (40-1) is achieved.

Similarly, the second output driver (50-2) illustrated in FIG. 8B includes a number of inverter stages ($INV_{b1}$, $INV_{b2}$, $INV_{b3}$, $INV_{b4}$, $INV_{b5}$, and $INV_{b6}$) configured to amplify the second modulated signal (40-2) and output the second push-pull output signal (52-2).

Figure 9:
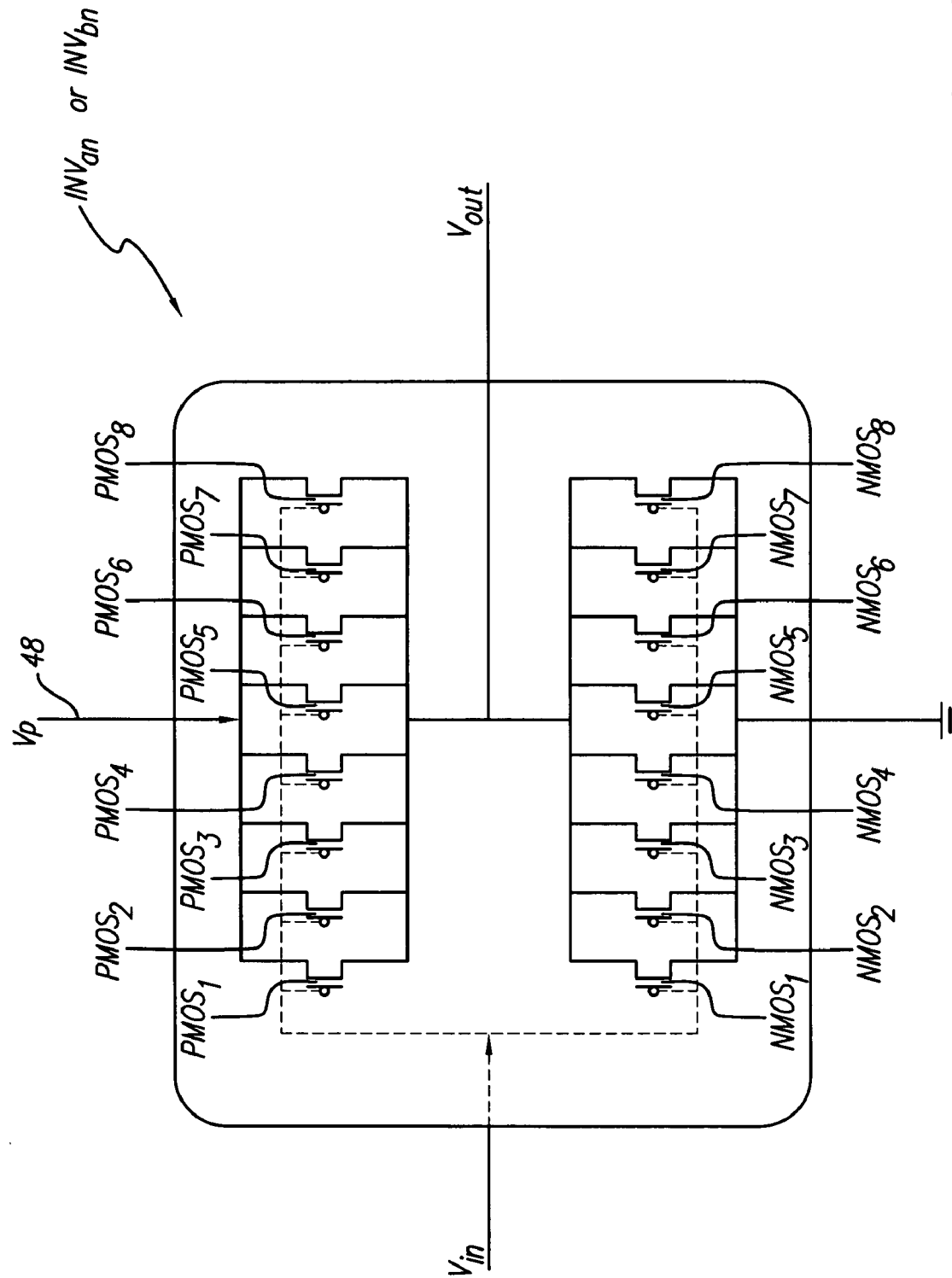
FIG. 9 illustrates a number of transistors included within each inverter stage shown in FIGS. 8A-8B according to principles described herein.

FIG. 9 illustrates a number of transistors included within each inverter stage shown in FIGS. 8A-8B. As shown in FIG. 9, each stage includes eight PMOS transistors ($PMOS_1$, $PMOS_2$, $PMOS_3$, $PMOS_4$, $PMOS_5$, $PMOS_6$, $PMOS_7$, and $PMOS_8$) and eight NMOS transistors ($NMOS_1$, $NMOS_2$, $NMOS_3$, $NMOS_4$, $NMOS_5$, $NMOS_6$, $NMOS_7$, and $NMOS_8$). A control signal $V_{in}$ controls the state of all of the transistors (also called switches). For example, when the control signal $V_{in}$ is zero or "low," the PMOS switches close and the NMOS switches open. This results in the power signal (48) being connected to the output $V_{out}$ of the stage. While the control signal $V_{in}$ is positive or "high," the PMOS switches open and the NMOS switches close, thereby connecting the output $V_{out}$ to ground. It will be recognized that any type of transistor or switch may be used in place of the PMOS and NMOS transistors. It will also be recognized that the size and number of PMOS and NMOS transistors may vary as best serves a particular application.

Hence, the amplifier (32; FIG. 5) may be used to efficiently provide power to both a first implantable device requiring a relatively high power level and a second implantable device requiring a relatively low power level. For example, the amplifier (32; FIG. 5) may be programmed via the power level control signal (42; FIG. 5) to operate in a high power mode to efficiently provide power to an implantable device requiring 50 to 200 mW. The amplifier (32; FIG. 5) may alternatively be programmed via the power level control signal (42; FIG. 5) to operate in a low power mode to efficiently provide power to an implantable device requiring 10 to 90 mW.

In some examples, it is desirable to use multiple amplifiers (32; FIG. 5) with wide dynamic ranges to provide power to one or more implanted devices. Some implantable devices include components in the same die or within the same integrated circuit that operate within different voltage or power ranges. For example, some implantable devices include components (e.g., transistors) that operate within a voltage range of zero to 1.8 volts, components that operate within a voltage range of zero to 3.3 volts, and components that operate within a voltage range of zero to 5.5 volts. However, each of these components has a range within which they operate most efficiently. For example, components operating within a range of zero to 3.3 volts may be most efficient within a range of 1.5 to 3.3 volts. Likewise, components operating within a range of zero to 5.5 volts may be most efficient within a range of 2.0 to 5.5 volts. It will be recognized that the voltage ranges within which components operate most efficiently may vary from component to component.

Figure 10:
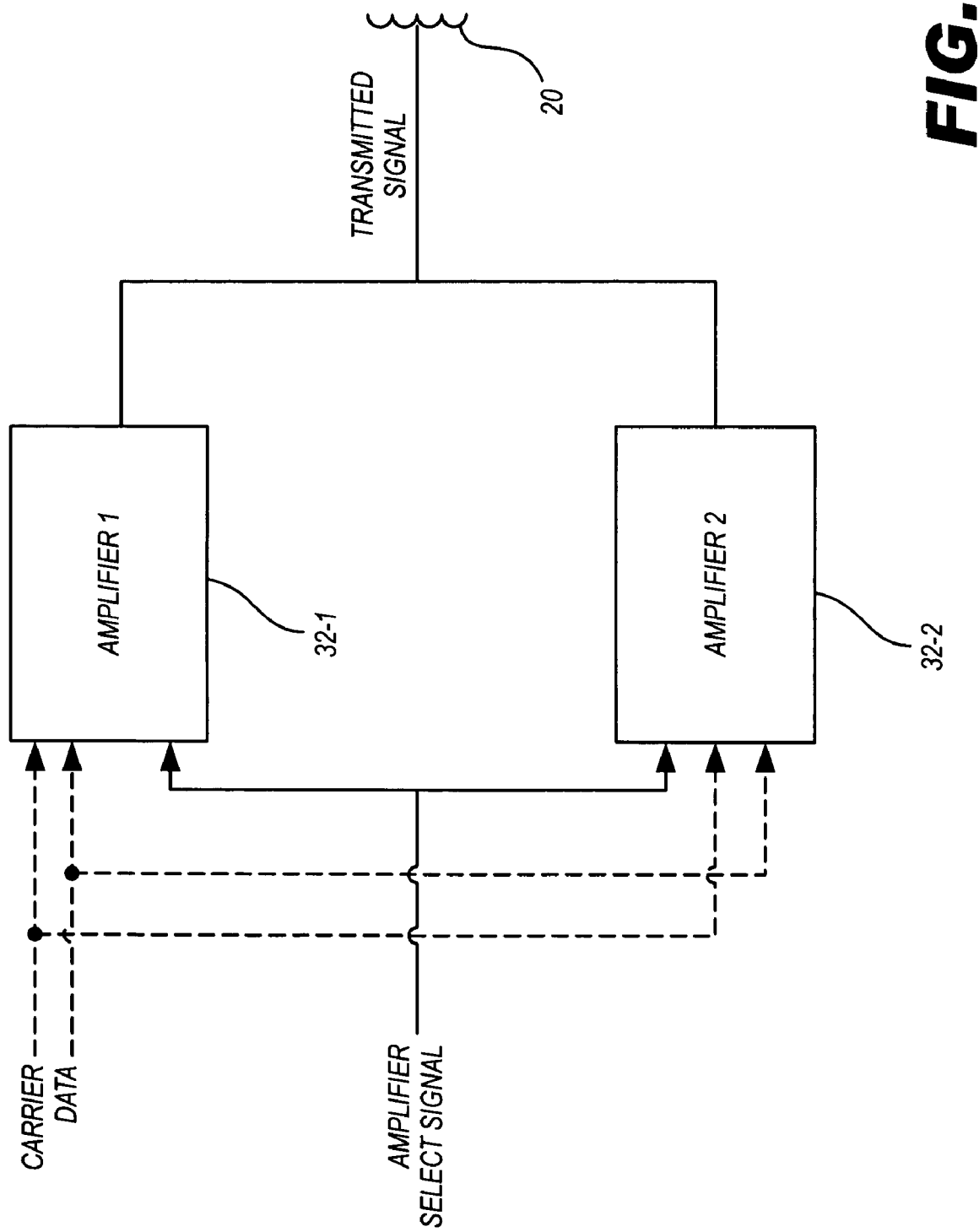
FIG. 10 illustrates an exemplary configuration wherein two amplifiers are used to provide power to one or more implantable devices having two different power range requirements according to principles described herein.

Hence, multiple amplifiers (32; FIG. 5) with wide dynamic ranges may be used to effectively provide power to one or more implanted devices operating within a number of different power ranges. FIG. 10 illustrates an exemplary configuration wherein two amplifiers (32-1, 32-2) are used to provide power to one or more implantable devices having two different power range requirements. For example, the first amplifier (32-1) may be configured to provide power to a number of components operating within a range of zero to 1.8 volts and the second amplifier (32-2) may be configured to provide power to a number of components operating within a range of 1.5 to 3.3 volts. It will be recognized that FIG. 10 shows two amplifiers (32) for illustrative purposes only and that any number of amplifiers (32) may be used as best serves a particular application. Each amplifier may be configured to support components operating over a corresponding different voltage or power range. It will also be recognized that the amplifiers (32) may be configured to operate within any voltage or power range as best serves a particular application.

Moreover, each amplifier (32) shown in FIG. 10 may include any number of output drivers (50; FIG. 5). For example, each amplifier (32) may include three or more output drivers (50; FIG. 5).

As shown in FIG. 10, the carrier and data signals are input into both amplifiers (32). An amplifier select signal controls which amplifier (32) is active. In other words, the amplifier select signal determines which amplifier (32) generates the signal that is transmitted to the implanted device. For example, if the implanted device being powered requires the voltage range provided by the first amplifier (32-1), the amplifier select signal activates the first amplifier (32-1) and deactivates (i.e., turns "off") the second amplifier (32-2).

In some examples, the amplifier select signal may include a number of logic bits configured to activate one of the amplifiers (e.g., 32-1) and deactivate the other amplifier (e.g., 32-2). Additionally, any other means of selectively activating and deactivating the amplifiers may be used. The amplifier select signal may selectively activate or deactivate any particular amplifier. For example, the amplifier select signal may activate the first amplifier (32-1) and deactivate the second amplifier (32-2) in order to provide power to a number of components operating within zero to 1.8 volts. Likewise, the amplifier select signal may activate the second amplifier (32-2) and deactivate the first amplifier (32-1) in order to provide power to a number of components operating within 1.5 to 3.3 volts. In some examples, more than one amplifier may be activated simultaneously depending on the number and power requirements of supported components being operated.

Figure 11:
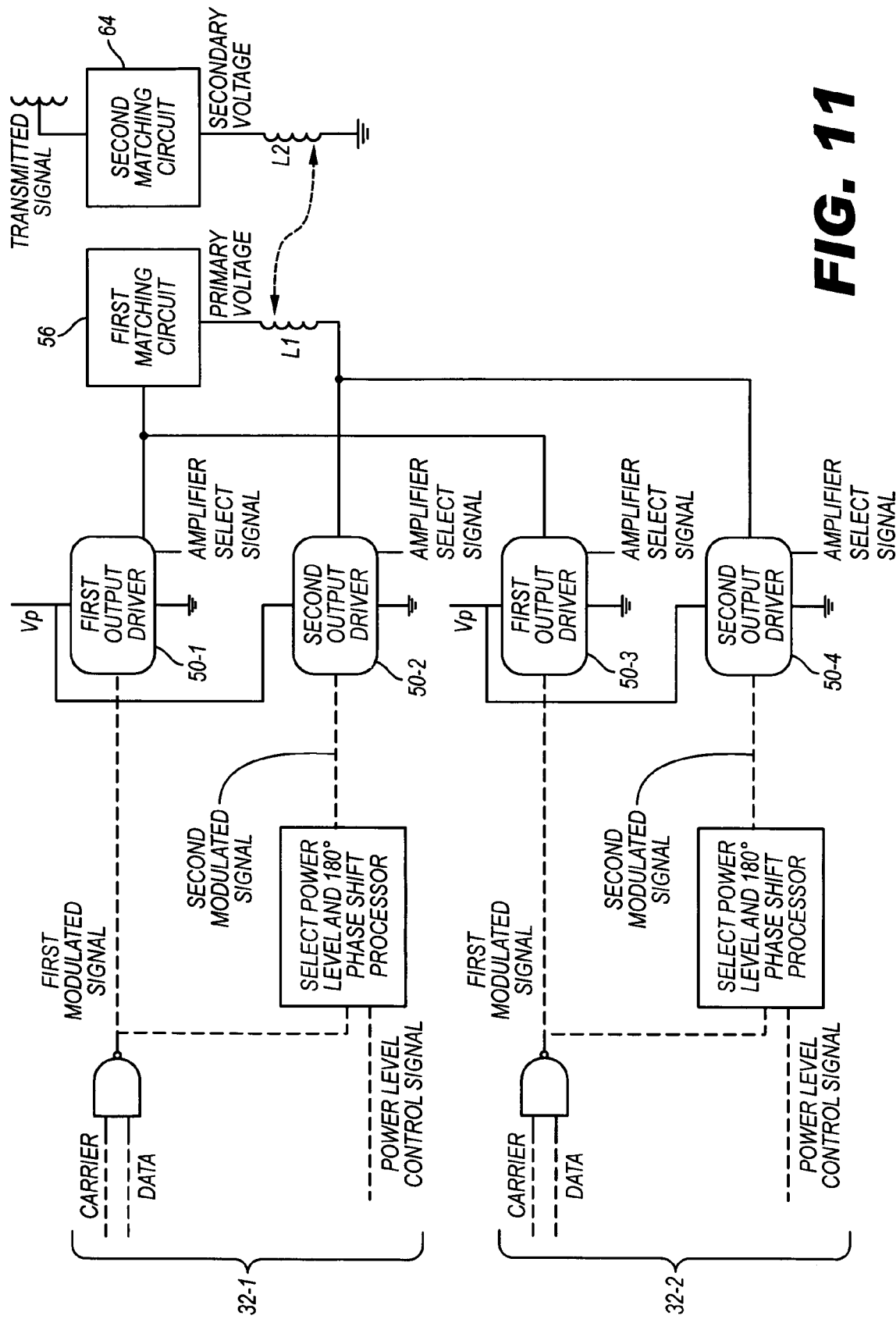
FIG. 11 is a more detailed diagram of the amplifiers of FIG. 10 according to principles described herein.

FIG. 11 is a more detailed diagram of the amplifiers (32) of FIG. 10. As shown in FIG. 11, the first and second output drivers (50-1 through 50-4) of each amplifier (32-1, 32-2) may be electrically coupled to the same first and second matching circuits (56, 64). Using the same matching circuits (56, 64) for each of the amplifiers (32) conserves die space, reduces overall power consumption, and reduces the overall size of the external device. However, it will be recognized that any number of matching circuits (56, 64) may be used with the amplifiers (32).

As shown in FIG. 11, the amplifier select signal may be input into each of the output drivers (50). As mentioned, the amplifier select signal is configured to deactivate one or more of the amplifiers (32) when their corresponding power ranges are not required by the implanted device. In order to deactivate an amplifier (32), both of its output drivers (e.g., 50-3, 50-4) are deactivated or disabled at substantially the same time. Hence, as will be described in more detail below, the amplifier select signal of FIG. 11 is configured to deactivate both the first and second output drivers (e.g., 50-3, 50-4) of an amplifier (e.g., 32-2) at substantially the same time.

As used herein and in the appended claims, the terms "disable" and "deactivate" and their derivatives will be used to refer to any action that turns "off" or disables the output signal of a device (e.g., an output driver or an amplifier).

Likewise, the terms "enable" and "activate" and their derivatives will be used herein and in the appended claims to refer to any action that turns "on" or enables the output signal of a device (e.g., an output driver or an amplifier).

Figure 12:
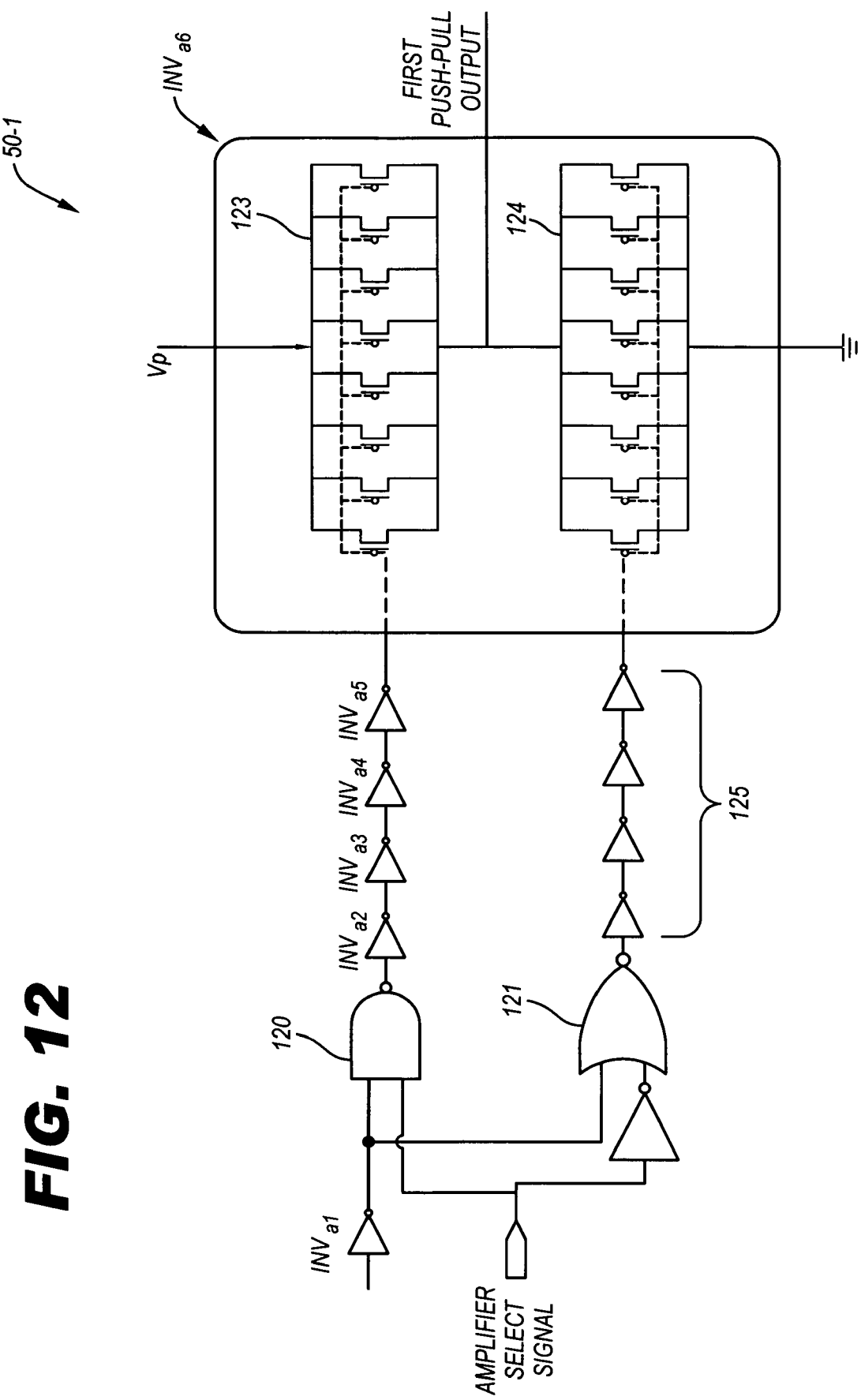
FIG. 12 shows the last modified inverter stage of the first output driver and exemplary circuitry that may be used to disable the output driver according to principles described herein.

In some examples, an output driver (50; FIG. 5) is deactivated or disabled by modifying the last inverter stage (e.g., $INV_{a6}$; FIG. 8A) and disabling the modified inverter stage. FIG. 12 shows the last inverter stage $INV_{a6}$ in modified form of the first output driver (50-1) and exemplary circuitry that may be used to disable the output driver (50-1). The output driver corresponding to the circuitry of FIG. 12 is the first output driver (50-1) of an amplifier for illustrative purposes only. It will be recognized that similar circuitry may be used to deactivate any output driver within an amplifier as best serves a particular application.

In some examples, the output driver (50-1) is disabled by simultaneously applying a "high" voltage (e.g., Vp or a "1") to the gates of the PMOS transistors (123) within the inverter stage $INV_{a6}$ and a "low" voltage (e.g., ground or a "0") to the gates of the NMOS transistors (124) within the inverter stage $INV_{a6}$.

Hence, as shown in FIG. 12, the input into the modified inverter stage $INV_{a6}$ is broken up into two inputs. The first input is connected to the gates of the PMOS transistors (123) and the second input is connected to the gates of the NMOS transistors (124). The first input includes the output of a NAND gate (120) passing through a series of inverter stages $INV_{a2}$ through $INV_{a5}$. As shown in FIG. 12, the NAND gate (120) has two inputs: the output from the first inverter stage $INV_{a1}$ and the amplifier select signal. In this configuration, the output of the NAND gate (120), and therefore the input into the gates of the PMOS transistors (123), is always "high" when the amplifier select signal is "0" or "low."

Likewise, the second input includes the output of a NOR gate (121) passing through a series of inverter stages (125). As shown in FIG. 12, the NOR gate (121) has two inputs: the output from the first inverter stage $INV_{a1}$ and the inverse of the amplifier select signal. In this configuration, the output of the NOR gate (121), and therefore the input into the gates of the NMOS transistors (124), is always "low" when the amplifier select signal is "0" or "low."

As mentioned, the push-pull output of the output driver (50-1) is disabled when a "high" voltage is input at the gates of the PMOS transistors (123) and a "low" voltage is input at the gates of the NMOS transistors (124). Hence, when the amplifier signal is "low," the push-pull output of the output driver (50-1) is disabled.

However, when the amplifier select signal is "high," the state of the inverter stage $INV_{a6}$ depends on the state of the input signal coming from $INV_{a5}$. In this manner, the output driver (50-1) may be activated by switching the amplifier select signal to "high."

Figure 13:
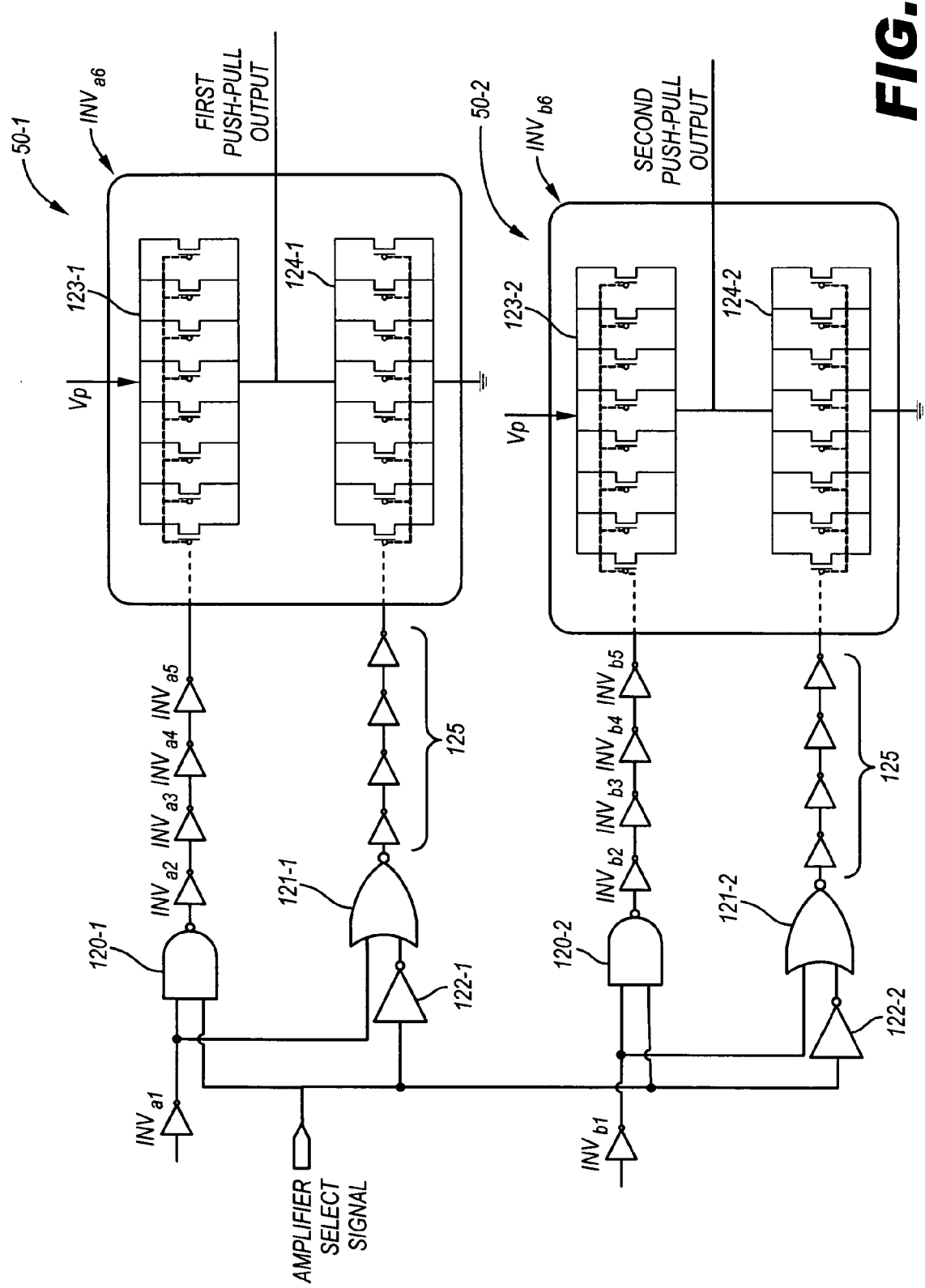
FIG. 13 illustrates exemplary circuitry that may be used to disable both the first and second output drivers of an amplifier according to principles described herein.

Hence, by breaking up the input into the last modified inverter stage and by using the circuitry shown in FIG. 12, the push-pull outputs of any number of output drivers (50) may be simultaneously disabled. For example, FIG. 13 illustrates exemplary circuitry that may be used to disable both the first and second output drivers (50-1, 50-2) of an amplifier. As shown in FIG. 13, the first output driver (50-1) is disabled by disabling a modified last inverter stage $INV_{a6}$ with the NAND gate (120-1), NOR gate (121-1), and inverter (122-1). Likewise, the second output driver (50-2) is disabled by disabling a modified last inverter stage $INV_{b6}$ with the NAND gate (120-2), NOR gate (121-2), and inverter (122-2).

It will be recognized that any other combination of digital logic, electronic circuitry, software, hardware, and firmware may be used to disable the first and second push-pull outputs of an amplifier as best serves a particular application.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
   providing an external device that comprises a first dynamic range amplifier and a second dynamic range amplifier, said first and second dynamic range amplifiers each comprising first and second output drivers;
   implanting a stimulator coupled to one or more electrodes within a patient;
   generatng an output signal based on a first input signal with said first output driver of said first dynamic range amplifier;
   generating an output signal based on a second input signal with said second output driver of said first dynamic range amplifier, said second input signal comprising a substantially 180-degree-phase-shifted version of said first input signal;
   generating an output signal based on said first input signal with said first output driver of said second dynamic range amplifier;
   generating an output signal based on said second input signal with said second output driver of said second dynamic range amplifier;
   selecting one of said dynamic range amplifiers to be used in generating a power signal for said stimulator;
   disabling a remaining number of said dynamic range amplifiers; and
   generating said power signal based on a combination of at least one of said output signals generated by said selected dynamic range amplifier;
   transmitting said power signal to said stimulator; and
   using said power signal to generate stimulation current and deliver said stimulation current to a stimulation site within said patient via said one or more electrodes.

2. The method of claim 1, further comprising:
   selectively indicating one of a low power mode and a high power mode;
   disabling said second output driver of said selected dynamic range amplifier when said low power mode is indicated; and
   enabling said second output driver of said selected dynamic range amplifier when said high power mode is indicated.

3. The method of claim 2, wherein said low power mode corresponds to a first power level and said high power mode corresponds to a second power level substantially equal to four times said first power level.

4. The method of claim 1, wherein said generating said power signal based on said output signals of said selected dynamic range amplifier comprises adding said output signal generated by said first output driver of said selected dynamic range amplifier to said output signal generated by said second output driver of said selected dynamic range amplifier.

5. The method of claim 1, wherein each of said output drivers comprises a number of inverter stages beginning with a first inverter stage and ending with a last modified inverter stage.

6. The method of claim 5, wherein said last modified inverter stage comprises a bank of PMOS transistors and a bank of NMOS transistors.

7. The method of claim 1, wherein said stimulator comprises at least one or more of a cochlear implant stimulator, a spinal cord stimulator, a microstimulator, a deep brain stimulator, and an implantable pulse generator.

8. An implantable stimulator system comprising:
an external device; and
a stimulator coupled to one or more electrodes and configured to be implanted within a patient;
wherein said external device comprises
first and second dynamic range amplifiers each comprising a first output driver configured to generate an output signal based on a first input signal and a second output driver configured to generate an output signal based on a second input signal, said second input signal comnrising a substantially 180-degree-phase-shifted version of said first input signal;
control circuitry configured to select one of said dynamic range amplifiers and disable a remaining number of said dynamic range amplifiers in accordance with an amplifier select signal;
a matching circuit communicatively coupled to said first and second dynamic range amplifiers and configured to generate said a power signal based on a combination of at least one of said output signals generated by said selected dynamic range amplifier; and
a primary coil communicatively coupled to said matching circuit and configured to transmit said power signal to said stimulator; and
wherein said stimulator comprises
a secondary coil configured to receive said power signal; and
circuitry configured to use said power signal to generate stimulation current and deliver said stimulation current to a stimulation site within said patient via said one or more electrodes.

9. The system of claim 8, wherein said external device further comprises:
a processor configured to receive a control signal input configured to selectively indicate one of a low power mode and a high power mode;
wherein said processor is further configured to disable said second output driver of said selected dynamic range amplifier when said control signal input indicates said low power mode and enable said second output driver of said selected dynamic range amplifier when said control signal input indicates said high power mode.

10. The system of claim 9, wherein said low power mode corresponds to a first power level and said high power mode corresponds to a second power level substantially equal to four times said first power level.

11. The system of claim 8, wherein said matching circuit comprises a first coil inductively coupled to a second coil.

12. The system of claim 8, wherein each of said output drivers comprises a number of inverter stages beginning with a first inverter stage and ending with a last modified inverter stage, wherein said last modified inverter stage is coupled to said control circuitry.

13. The system of claim 12, wherein said last modified inverter stage comprises a bank of PMO)S transistors and a bank of NMOS transistors, wherein said control circuitry is configured to disable said last modified inverter stage by applying a logic high signal to a gate input of each of said PMOS transistors and a logic low signal to a gate input of each of said NMOS transistors.

14. The system of claim 8, wherein said stimulator comprises at least one or more of a cochlear implant stimulator, a spinal cord stimulator, a microstimulator, a deep brain stimulator, and an implantable pulse generator.

15. The system of claim 8, wherein said output signals generated by said second dynamic range amplifier have an amplitude greater than an amplitude of said output signals generated by said first dynamic range amplifier.

16. The system of claim 8, wherein said external device comprises a signal processor.

17. A system comprising:
an external device; and
a stimulator coupled to one or more electrodes and configured to be implanted within a patient;
wherein said external device comprises
first and second dynamic range amplifiers each comprising a first output driver configured to generate an output signal based on a first input signal and a second output driver configured to generate an output signal based on a second input signal, said second input signal comprising a substantially 180-degree-phase-shifted version of said first input signal;
means for selecting one of said dynamic range amplifiers to be used in generating a power signal for said stimulator;
means for disabling a remaining number of said amplifiers; and
means for generating said power signal based on a combination of at least one of said output signals generated by said selected dynamic range amplifier; and
means for transmitting said power signal to said stimulator; and
wherein said stimulator comprises means for using said power signal to generate stimulation current and deliver said stimulation current to a stimulation site within said patient via said one or more electrodes.

18. The system of claim 17, further comprising means for selectively indicating one of a low power mode or a high power mode.

* * * * *

UNITED STATES PATENT AND TRADEMARK OFFICE
CERTIFICATE OF CORRECTION

PATENT NO. : 7,254,449 B2
APPLICATION NO. : 11/341066
DATED : August 7, 2007
INVENTOR(S) : Rankiri Tissa Karunasiri It is certified that error appears in the above-identified patent and that said Letters Patent is hereby corrected as shown below:

On the front page of the patent, after the inventor information (item 76), please add --Assignee: Advanced Bionics Corporation, Valencia, CA (US)--.

Signed and Sealed this

Eighth Day of January, 2008

JON W. DUDAS
*Director of the United States Patent and Trademark Office*